(12) United States Patent
Kruse et al.

(10) Patent No.: US 7,262,034 B2
(45) Date of Patent: Aug. 28, 2007

(54) PROCESS FOR THE FERMENTATIVE PREPARATION OF D-PANTOTHENIC ACID AND/OR SALTS THEREOF

(75) Inventors: Daniela Kruse, Bielefeld (DE); Georg Thierbach, Bielefeld (DE)

(73) Assignee: Degussa AG, Dusseldorf (DE)

( * ) Notice: Subject to any disclaimer, the term of this patent is extended or adjusted under 35 U.S.C. 154(b) by 341 days.

(21) Appl. No.: 10/480,486

(22) PCT Filed: May 31, 2002

(86) PCT No.: PCT/EP02/05960

§ 371 (c)(1),
(2), (4) Date: Dec. 15, 2003

(87) PCT Pub. No.: WO03/004672

PCT Pub. Date: Jan. 16, 2003

(65) Prior Publication Data

US 2004/0152173 A1    Aug. 5, 2004

(30) Foreign Application Priority Data

May 31, 2002    (DE) .............................. 101 32 178

(51) Int. Cl.
*C12P 13/04* (2006.01)
*C12N 9/00* (2006.01)
*C12N 1/20* (2006.01)
*C07K 1/00* (2006.01)
*C07H 21/04* (2006.01)

(52) U.S. Cl. .................. 435/106; 435/41; 435/183; 435/195; 435/219; 435/252.3; 435/320.1; 530/350; 536/23.2

(58) Field of Classification Search ................. 435/41, 435/106, 183, 195, 219, 252.3, 320.1; 530/350; 536/23.2
See application file for complete search history.

(56) References Cited

U.S. PATENT DOCUMENTS

| | | | |
|---|---|---|---|
| 4,665,099 A * | 5/1987 | Ramallo et al. | ............ 514/763 |
| 5,518,906 A | 5/1996 | Hikichi et al. | |
| 6,184,007 B1 | 2/2001 | Dusch et al. | |
| 6,238,714 B1 | 5/2001 | Binder et al. | |

FOREIGN PATENT DOCUMENTS

| | | |
|---|---|---|
| EP | 0 493 060 | 7/1992 |
| EP | 0 590 857 | 4/1994 |
| EP | 1 006 192 | 6/2000 |
| WO | WO96/33283 | 10/1996 |
| WO | WO 97/10340 | 3/1997 |
| WO | WO97/10340 | 3/1997 |
| WO | WO 01/021772 | 3/2001 |
| WO | WO 02/061108 | 8/2002 |

OTHER PUBLICATIONS

Notification of the Recording of a Change (PCT/IB/306) issued for PCT/EP02/05960 (Mar. 1994).

* cited by examiner

*Primary Examiner*—Tekchand Saidha
*Assistant Examiner*—Christian L. Fronda
(74) *Attorney, Agent, or Firm*—Smith, Gambrell & Russell, LLP

(57) ABSTRACT

The invention provides a process for the fermentative preparation of D-pantothenic acid and/or salts thereof or feedstuffs additives comprising these by fermentation of microorganisms of the Bacillus group, in particular those which already produce D-pantothenic acid, which comprises enhancing, in particular over-expressing, in the microorganisms one or more of the nucleotide sequence(s) which code(s) for the gene or ORF serA, serC, ywpJ or glyA.

12 Claims, No Drawings

US 7,262,034 B2

PROCESS FOR THE FERMENTATIVE PREPARATION OF D-PANTOTHENIC ACID AND/OR SALTS THEREOF

FIELD OF THE INVENTION

This invention relates to a process for the fermentative preparation of D-pantothenic acid and/or salts thereof or mixtures comprising these using microorganisms of the Bacillus group in which at least one or more of the genes or open reading frames (ORF) chosen from the group consisting of serA, serC, ywpJ and glyA is or are enhanced.

PRIOR ART

Pantothenic acid is produced worldwide in an order of magnitude of several thousand tonnes a year. It is used inter alia in human medicine, in the pharmaceuticals industry and in the foodstuffs industry. A large portion of the pantothenic acid produced is used for nutrition of stock animals such as poultry and pigs.

Pantothenic acid can be prepared by chemical synthesis, or biotechnologically by fermentation of suitable microorganisms in suitable nutrient solutions. In the chemical synthesis, DL-pantolactone is an important precursor. It is prepared in a multi-stage process from formaldehyde, isobutylaldehyde and cyanide, and in further process steps, the racemic mixture is separated, D-pantolactone is subjected to a condensation reaction with β-alanine, and D-pantothenic acid is obtained in this way.

A typical commercial form is the calcium salt of D-pantothenic acid. The calcium salt of the racemic mixture of D,L-pantothenic acid is also customary.

The advantage of the fermentative preparation by microorganisms lies in the direct formation of the desired stereoisomeric form, that is to say the D-form, which is free from L-pantothenic acid.

Various species of bacteria, such as e.g. *Escherichia coli* (*E. coli*), *Arthrobacter ureafaciens*, *Corynebacterium erythrogenes*, *Brevibacterium ammoniagenes*, *Corynebacterium glutamicum*, *Bacillus subtilis* and also yeasts, such as e.g. *Debaromyces castellii* can produce D-pantothenic acid.

Instructions for improving the fermentative production processes are, for example, EP-A 0 493 060, EP-A-0590857, U.S. Pat. No. 5,518,906, WO97/10340, WO01/21772 or U.S. Pat. No. 6,184,007.

After fermentation, the D-pantothenic acid or the corresponding salt is isolated from the fermentation broth and purified (EP-A-0590857 and WO96/33283). The fermentation broth containing D-pantothenic acid can also be dried with the biomass produced during the fermentation (U.S. Pat. No. 6,238,714) and then used in particular as a feedstuffs additive.

OBJECT OF THE INVENTION

The inventors had the object of providing new measures for improved fermentative preparation of D-pantothenic-acid and/or salts thereof, and animal feedstuffs additives comprising these.

SUMMARY OF THE INVENTION

When D-pantothenic acid or pantothenic acid or pantothenate are mentioned in the following text, this means not only the free acids but also the salts of D-pantothenic acid, such as e.g. the calcium, sodium, ammonium or potassium salt.

The invention provides a process for the fermentative preparation of D-pantothenic acid and/or salts thereof using microorganisms of the Bacillus group which in particular already produce D-pantothenic acid and in which at least one or more of the nucleotide sequence(s) which code(s) for the serA gene, serC gene, ywpJ-ORF, and glyA gene is or are enhanced, in particular over-expressed.

In particular, the process is a process which comprises carrying out the following steps:

a) fermentation of microorganisms of the Bacillus group in which at least one or more of the genes or open reading frames chosen from the group consisting of serA, serc, ywpJ and glyA is or are enhanced, in particular over-expressed, optionally in combination with the attenuation or enhancement of further genes or open reading frames.

b) optionally in the presence of alkaline earth metal compounds, these being added to the fermentation broth continuously or discontinuously in preferably stoichiometric amounts c) concentration of the D-pantothenic acid or the corresponding salts in the medium or the fermentation broth or optionally in the cells of the microorganisms of the Enterobacteriaceae family and d) after conclusion of the fermentation, isolation of the D-pantothenic acid, and/or of the corresponding salt(s).

The invention also provides a process in which, after conclusion of the fermentation, some or all (0 to 100%) of the biomass remains in the fermentation broth, and the broth obtained in this way is processed, optionally after concentration, to a solid mixture which comprises D-pantothenic acid and/or salts thereof and optionally comprises further constituents of the fermentation broth.

DETAILED DESCRIPTION OF THE INVENTION

The term "enhancement" in this connection describes the increase in the intracellular activity of one or more enzymes or proteins in a microorganism which are coded by the corresponding DNA, for example by increasing the number of copies of the gene or genes, of the open reading frame (ORF) or ORFs, using a potent promoter or a gene or allele or ORF which codes for a corresponding enzyme or protein with a high activity, and optionally combining these measures.

Open reading frame (ORF) describes a section of a nucleotide sequence which codes or can code for a protein or polypeptide or ribonucleic acid to which no function can be assigned according to the prior art. After assignment of a function to the nucleotide sequence section in question, it is in general referred to as a gene.

By enhancement measures, in particular over-expression, the activity or concentration of the corresponding protein is in general increased by at least 10%, 25%, 50%, 75%, 100%, 150%, 200%, 300%, 400% or 500%, up to a maximum of 1000% or 2000%, based on that of the wild-type protein or the activity or concentration of the protein in the starting microorganism.

The microorganisms which the present invention provides can produce D-pantothenic acid from glucose, sucrose, lactose, fructose, maltose, molasses, starch, cellulose or from glycerol and ethanol. They are representatives of the Bacillus group, in particular of the genus Bacillus, preferably the species *Bacillus subtilis*.

The Bacillus group includes, inter alia, *Bacillus subtilis, Bacillus lentimorbus, Bacillus lentus, Bacillus firmus, Bacillus pantothenticus, Bacillus amyloliquefaciens, Bacillus cereus, Bacillus circulans, Bacillus coagulans, Bacillus licheniformis, Bacillus megaterium, Bacillus pumilus, Bacillus thuringiensis, Bacillus halodurans, Bacillus brevis, Bacillus stearothermophilus Bacillus pulvifaciens* and other so-called group 1 Bacillus species which are characterized by the corresponding 16S rRNA type (Priest (1993), In: *Bacillus subtilis* and Other Gram-Positive Bacteria, eds. Sonenshein et al., ASM, Washington, D.C., USA).

Suitable D-pantothenic acid-producing strains of the Bacillus group, in particular of the species *Bacillus subtilis*, are inter alia, for example, the strains mentioned in WO01/21772

*Bacillus subtilis* strain PA 221
*Bacillus subtilis* strain PA 248
*Bacillus subtilis* strain PA 236
*Bacillus subtilis* strain PA 221/pAN429-4
*Bacillus subtilis* strain PA 413-4
*Bacillus subtilis* strain PA 236-1
*Bacillus subtilis* strain PA 340
*Bacillus subtilis* strain PA 377
*Bacillus subtilis* strain PA 365
*Bacillus subtilis* strain PA 377-2
*Bacillus subtilis* strain PA824-2.

It has been found that microorganisms of the Bacillus group produce D-pantothenic acid in an improved manner after enhancement, in particular over-expression, of one or more of the genes or ORFs, or of the nucleotide sequences which code for these, chosen from the group consisting of serA, serC, ywpJ and glyA.

The nucleotide sequences of the genes or open reading frames (ORF) of *Bacillus subtilis* belong to the prior art and can also be found in the genome sequence of *Bacillus subtilis* published by Kunst et al. (Nature 390, 249-256 (1997).

serA:
  Description: Phosphoglycerate dehydrogenase
  EC No.: 1.1.1.95
  Reference: Sorokin et al., Molecular Microbiology 10:385-395 (1993)
  Accession No.: L47648 serC:
  Description: Phosphoserine aminotransferase
  Alternative gene name: yhaF
  EC No.: 2.6.1.52
  Reference: Noback et. al., Microbiology 144:859-875 (1998)
  Accession No.: Z99109 ywpJ:
  Description: Open reading frame of unknown function
  Reference: Kunst et. al., Nature 390: 249-256 (1997)
  Accession No.: Z83337 glyA gene:
  Description: Serine hydroxymethyltransferase, serine methylase
  Alternative gene name: glyC, ipc-34d
  EC No.: 2.1.2.1
  Reference: Kunst et. al., Nature 390: 249-256 (1997)
  Accession No.: Z99122.

The nucleic acid sequences can be found in the databanks of the National Center for Biotechnology Information (NCBI) of the National Library of Medicine (Bethesda, Md., USA), the nucleotide sequence databank of the European Molecular Biologies Laboratories (EMBL, Heidelberg, Germany or Cambridge, UK) or the DNA databank of Japan (DDBJ, Mishima, Japan).

The genes or open reading frames described in the text references mentioned can be used according to the invention. Alleles of the genes or open reading frames which result from the degeneracy of the genetic code or due to sense mutations of neutral function can furthermore be used.

In the same way, nucleic acids or polynucleotides which code for proteins or polypeptides which are identical, homologous or similar to the extent of at least 40%, 50%, 60%, 70%, 80%, 85%, 90%, 95%, 96%, 97%, 98%, 99% or 100%, originate from strains of the Bacillus group and have the corresponding function can be used.

To achieve an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative D-pantothenic acid production. The expression is likewise improved by measures to prolong the life of the m-RNA. Furthermore, the enzyme activity is also increased by preventing the degradation of the enzyme protein. The genes or gene constructs can either be present in plasmids with a varying number of copies, or can be integrated and amplified in the chromosome. Alternatively, an over-expression of the genes in question can furthermore be achieved by changing the composition of the media and the culture procedure.

A strain transformed with one or more plasmid vectors, in particular expression vectors, wherein the plasmid vector(s) carries (carry) at least one of the nucleotide sequences which code for the genes or open reading frames serA, serC, ywpJ and glyA, can be employed in a process according to the invention.

In a further process according to the invention, the ribosome binding sites of one or more of the genes or open reading frames chosen from the group consisting of serA, serC, ywpJ and glyA can be optimized.

In a further process according to the invention, an additional promoter can be placed in front of one or more of the genes or open reading frames chosen from the group consisting of serA, serC, ywpJ and glyA.

In a further process according to the invention, at least one further copy of one or more of the genes or open reading frames chosen from the group consisting of serA, serC, ywpJ and glyA can be added to the chromosome of the host.

It may furthermore be advantageous for the production of D-pantothenic acid with strains of the Bacillus group, in addition to enhancement of one or more of the genes or open reading frames chosen from the group consisting of serA, serC, ywpJ and glyA, for one or more of the genes chosen from the group consisting of the panE gene which codes for ketopantoate reductase (WO/0121772)
  the polypeptide coded by the open reading frame ylbQ or the apbA gene (Kunst et. al. Nature 20; 390(6657):249-256 (1997); Accession No. Z99111)
  the panB gene which codes for ketopantoate hydroxymethyltransferase (Sorokin et al., Microbiology 142: 2005-2016 (1996); WO01/21772; Accession No.: L47709)

the panD gene which codes for aspartate 1-decarboxylase (Sorokin et al., Microbiology 142:2005-2016 (1996); WO01/21772; Accession No.: L47709)

the panC gene which codes for pantothenate synthetase (Sorokin et al., Microbiology 142:2005-2016 (1996); WO01/21772; Accession No.: L47709)

the ilvB and ilvN genes which code for acetohydroxy acid synthetase (Wipat et. al., Microbiology 142:3067-3078 (1996); Accession No.: Z75208)

the alsS gene which codes for α-acetolactate synthase (Renna et al., Journal of Bacteriology 175:3863-3875 (1993); Accession No.: Z93767)

the ilvC gene which codes for acetohydroxy acid isomeroreductase (Wipat et. al., Microbiology 142:3067-3078 (1996); Accession No.: Z75208)

the ilvD gene which codes for dihydroxy acid dehydratase (Sorokin et al., Microbiology 142:2005-2016 (1996); Accession No.: Z99115)

to be enhanced, in particular over-expressed, individually or together.

Finally, it may be advantageous for the production of D-pantothenic acid with strains of the Bacillus group, in addition to enhancement of one or more of the genes or open reading frames chosen from the group consisting of serA, serC, ywpJ and glyA, or nucleotide sequences which code for these, for one or more of the genes or open reading frames chosen from the group consisting of the protein coded by ywaA-ORF (Glaser et al., Molecular Microbiology 10:371-384 (1993); Accession No. Z49992)

the protein coded by ybgE-ORF (Kunst et al., Nature 390, 249-256 (1997); Accession No. Z99105)

the ansB gene which codes for L-aspartase (Sun and Seflow, Journal of Bacteriology 173:3831-3845 (1991); Accession No.: D84432)

the alsD gene which codes for acetolactate decarboxylase (Renna et al., Journal of Bacteriology 175:3863-3875 (1993); Accession No.: Z93767)

the coaA gene which codes for pantothenic acid kinase (Kunst et al., Nature 390, 249-256 (1997); Accession No.: Z99116)

the coax gene which codes for coax-pantothenic acid kinase, or yacB-ORF (Kunst et al., Nature 390, 249-256 (1997); Accession No.: Z99104; WO01/21772)

to be attenuated, in particular eliminated or expressed at a low level, individually or together.

The term "attenuation" in this connection describes the reduction or elimination of the intracellular activity of one or more enzymes (proteins) in a microorganism which are coded by the corresponding DNA, for example by using a weak promoter or using a gene or allele or ORF which codes for a corresponding enzyme (protein) with a low activity or inactivates the corresponding gene or ORF or enzyme (protein) and optionally combining these measures.

The reduction in gene expression can take place by suitable culturing, by genetic modification (mutation) of the signal structures of gene expression or also by the antisense-RNA technique. Signal structures of gene expression are, for example, repressor genes, activator genes, operators, promoters, attenuators, ribosome binding sites, the start codon and terminators.

Mutations which lead to a change or reduction in the catalytic properties of enzyme proteins are known from the prior art.

Possible mutations are transitions, transversions, insertions and deletions. Depending on the effect of the amino acid exchange on the enzyme activity, "missense mutations" or "nonsense mutations" are referred to. Insertions or deletions of at least one base pair in a gene lead to "frame shift mutations", which lead to incorrect amino acids being incorporated or translation being interrupted prematurely. If a stop codon is formed in the coding region as a consequence of the mutation, this also leads to a premature termination of the translation Deletions of several codons typically lead to a complete loss of the enzyme activity.

By attenuation measures, the activity or concentration of the corresponding protein is in general reduced to 0 to 75%, 0 to 50%, 0 to 25%, 0 to 10% or 0 to 5% of the activity or concentration of the wild-type protein or of the activity or-concentration of the protein in the starting microorganism.

It may furthermore be advantageous for the production of D-pantothenic acid, in addition to over-expression of one or more of the genes or open reading frames chosen from the group consisting of serA, serC, ywpJ and glyA, to eliminate undesirable side reactions (Nakayama: "Breeding of Amino Acid Producing Microorganisms", in: Overproduction of Microbial Products, Krumphanzl, Sikyta, Vanek (eds.), Academic Press, London, UK, 1982). Bacteria in which the metabolic pathways which reduce the formation of D-pantothenic acid are at least partly eliminated can be employed in the process according to the invention.

The microorganisms produced according to the invention can be cultured in the batch process (batch culture), the fed batch (feed process) or the repeated fed batch process (repetitive feed process). A summary of known culture methods is described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991)) or in the textbook by Storhas (Bioreaktoren und periphere Einrichtungen [Bioreactors and Peripheral Equipment] (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981). The media described in WO01/21772 can also be used. Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substance can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and-ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as e.g. magnesium sulfate or iron sulfate, which are necessary for growth. Finally, essential growth substances, such as amino acids and vitamins, can be employed in addition to the abovementioned substances.

Precursors of pantothenic acid, such as aspartate, β-alanine, ketoisovalerate, ketopantoic acid or pantoic acid and optionally salts thereof, can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture.

For the preparation of alkaline earth metal salts of pantothenic acid, in particular the calcium salt or magnesium salt, it is equally possible to add the suspension or solution of an inorganic compound containing an alkaline earth metal, such as, for example, calcium hydroxide or MgO, or of an organic compound, such as the alkaline earth metal salt of an organic acid, for example calcium acetate, continuously or discontinuously during the fermentation. For this purpose, the cation necessary for preparation of the desired alkaline earth metal salt of D-pantothenic acid is introduced into the fermentation broth directly in the desired amount, preferably in an amount of 0.95 to 1.1 equivalents.

However, the salts can also be formed after conclusion of the fermentation by addition of the inorganic or organic compounds to the fermentation broth, from which the biomass has optionally been removed beforehand.

Antifoams, such as e.g. fatty acid polyglycol esters, can be employed to control the development of foam. Suitable substances having a selective action, e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 15° C. to 95° C., in particular 15° C. to 70° C., preferably 20° C. to 55° C., very particularly preferably 30° C. to 50° C. or 30° C. to 45° C. Culturing is continued until a maximum of D-pantothenic acid has formed. This target is usually reached within 10 hours to 160 hours.

The D-pantothenic acid or the corresponding salts of D-pantothenic acid contained in the fermentation broth can then be isolated and purified in accordance with the prior art.

It is also possible for the fermentation broths comprising D-pantothenic acid and/or salts thereof preferably first to be freed from all or some of the biomass by known separation methods, such as, for example, centrifugation, filtration, decanting or a combination thereof. However, it is also possible to leave the biomass in its entirety in the fermentation broth. In general, the suspension or solution is preferably concentrated and then worked up to a powder, for example with the aid of a spray dryer or a freeze-drying unit. This powder in then in general converted by suitable-compacting or granulating processes, e. g. also build-up granulation, into a coarser-grained, free-flowing, storable and largely dust-free product with a particle size distribution of preferably 20 to 2000 μm, in particular 100 to 1400 μm. In the granulation or compacting it is advantageous to employ conventional organic or inorganic auxiliary substances or carriers, such as starch, gelatine, cellulose derivatives or similar substances, such as are conventionally used as binders, gelling agents or thickeners in foodstuffs or feedstuffs processing, or further substances, such as, for example, silicas, silicates or stearates.

Alternatively, the fermentation product, with or without further of the conventional fermentation constituents, can be absorbed on to an organic or inorganic carrier substance which is known and conventional in feedstuffs processing, such as, for example, silicas, silicates, grits, brans, meals, starches, sugars or others, and/or stabilized with conventional thickeners or binders. Use examples and processes in this context are described in the literature (Die Mühle+ Mischfuttertechnik 132 (1995) 49, page 817).

D-Pantothenic acid and/or the desired salt of D-pantothenic acid or a formulation comprising these compounds is optionally added in a suitable process stage during or after the fermentation in order to achieve or establish the content of pantothenic acid desired in the product or the desired salt.

The desired content of pantothenic acid and/or the desired salt is in general in the range from 20 to 80 wt. % (based on the total dry weight).

The concentration of pantothenic acid can be determined with known chemical (Velisek; Chromatographic Science 60, 515-560 (1992)) or microbiological methods, such as e.g. the Lactobacillus plantarum test (DIFCO MANUAL, 10$^{th}$ Edition, p. 1100-1102; Michigan, USA).

What is claimed is:

1. A process for the improved production of at least one of D-pantothenic acid and an alkaline earth metal salt thereof, comprising:
    a) fermenting, in a fermentation broth, microorganisms of the Bacillus group selected from the group consisting of *Bacillus subtilis, Bacillus lentimorbus, Bacillus lentus, Bacillus firmus, Bacillus pantothenticus, Bacillus amyloliquefaciens, Bacillus cereus, Bacillus circulans, Bacillus coagulans, Bacillus licheniformis, Bacillus megaterium, Bacillus pumilus, Bacillus thuringiensis, Bacillus halodurans, Bacillus brevis, Bacillus stearothermophilus*, and *Bacillus pulvifaciens*, in which at least one nucleotide sequence from *Bacillus subtilis* which encodes a protein selected from the group consisting of phosphoserine aminotransferase, phosphoglycerate dehydrogenase and serine hydroxymethyltransferase is overexpressed, wherein the microorganisms produce D-pantothenic acid before the nucleotide sequence is overexpressed, and
    b) concentrating the D-pantothenic acid and/or salts thereof in the fermentation broth or in the microorganisms.

2. A process as claimed in claim 1, wherein the microorganisms are fermented in the presence of alkaline earth metal salts which are added continuously or discontinuously.

3. A process as claimed in claim 1 or 2, wherein the microorganisms are *Bacillus subtilis*.

4. A process as claimed in claim 1, wherein at least one polynucleotide selected from the group consisting of:
    4.1 the panE polynucleotide which codes for ketopantoate reductase,
    4.2 the panB polynucleotide which codes for ketopantoate hydroxymethyltransferase,
    4.3 the panD polynucleotide which codes for aspartate decarboxylase,
    4.4 the panC polynucleotide which codes for pantothenate synthetase,
    4.5 the ilvB and ilvN polynucleotides which code for acetohydroxy acid synthetase,
    4.6 the alsS polynucleotide which codes for α-acetolactate synthase,
    4.7 the ilvC polynucleotide which codes for acetohydroxy acid isomeroreductase, and
    4.8 the ilvD polynucleotide which codes for dihydroxy acid dehydratase is additionally overexpressed.

5. A process as claimed in claim 1, wherein at least one polynucleotide selected from the group consisting of:

5.1 the ansB polynucleotide which codes for L-aspartase,
5.2 the alsD polynucleotide which codes for acetolactate decarboxylase,
5.3 the coaA polynucleotide which codes for pantothenic acid kinase, and
5.4 the coaX polynucleotide which codes for coaX-pantothenic acid kinase is additionally attenuated.

6. A process as claimed in claim 1, wherein over-expression is achieved by at least one measure selected from the group consisting of use of a plasmid vector, optimization of the ribosome binding site, use of an additional promoter and incorporation of at least one additional gene copy.

7. The process according to claim 1, further comprising isolating the D-pantothenic acid and/or salts thereof.

8. The process according to claim 2, wherein the alkaline earth metal salts are added in stoichiometric amounts equivalent to the D-pantothenic acid formed.

9. The process according to claim 2, further comprising recovering alkaline earth metal salts of D-pantothenic acid.

10. A process for the preparation of feedstuffs additive comprising D-pantothenic acid and/or salts thereof by fermentation comprising:
    a) fermenting, in a fermentation broth, microorganisms of the Bacillus group selected from the group consisting of *Bacillus subtilis, Bacillus lentimorbus, Bacillus lentus, Bacillus firmus, Bacillus pantothenticus, Bacillus amyloliquefaciens, Bacillus cereus, Bacillus circulans, Bacillus coagulans, Bacillus licheniformis, Bacillus megaterium, Bacillus pumilus, Bacillus thuringiensis, Bacillus halodurans, Bacillus brevis, Bacillus stearothermophilus,* and *Bacillus pulvifaciens,* in which at least one nucleotide sequence from *Bacillus subtilis* which encodes a protein selected from the group consisting of phosphoserine aminotransferase, phosphoglycerate dehydrogenase and serine hydroxymethyltransferase is overexpressed, wherein the microorganisms produce D-pantothenic acid before the nucleotide sequence is overexpressed, and
    b) optionally concentrating the D-pantothenic acid and/or salts thereof in the fermentation broth or in cells of the microorganisms,
    c) optionally separating at least some resulting biomass and/or a portion of constituents from a D-pantothenic acid-containing fermentation broth resulting from the fermenting,
    d) converting a resulting D-pantothenic acid and/or salts thereof into a feedstuffs additive,
    e) converting the feedstuffs additive into a free-flowing form, and
    f) obtaining a free-flowing animal feedstuffs additive with a particle size distribution of 20 to 2000 µm.

11. A process as claimed in claim 10, wherein the particle size distribution is obtained by:
    a) drying and compacting, or
    b) spray drying, or
    c) spray drying and granulation, or
    d) spray drying and build-up granulation.

12. A process for the preparation of feedstuffs additive comprising at least one D-pantothenic salt selected from the group consisting of magnesium and calcium, said method comprising:
    a) fermenting, in a fermentation broth, microorganisms of the Bacillus group selected from the group consisting of *Bacillus subtilis, Bacillus lentimorbus, Bacillus lentus, Bacillus firmus, Bacillus pantothenticus, Bacillus amyloliquefaciens, Bacillus cereus, Bacillus circulans, Bacillus coagulans, Bacillus licheniformis, Bacillus megaterium, Bacillus pumilus, Bacillus thuringiensis, Bacillus halodurans, Bacillus brevis, Bacillus stearothermophilus,* and *Bacillus pulvifaciens,* in which at least one nucleotide sequence from *Bacillus subtilis* which encodes a protein selected from the group consisting of phosphoserine aminotransferase, phosphoglycerate dehydrogenase and serine hydroxymethyltransferase is overexpressed, wherein the microorganisms produce D-pantothenic acid before the nucleotide sequence is overexpressed, and
    b) optionally removing water from the fermentation broth,
    c) removing an amount of a biomass formed during the fermentation,
    d) optionally adding an amount of at least one of calcium and magnesium to the fermentation broth obtained according to b) and c), the amount of calcium and/or magnesium added being such that the total concentration thereof in the resulting feedstuffs additive is in the range from 20 to 80 wt. %,
    e) converting the resulting D-pantothenic salt into the feedstuffs additive, and
    f) obtaining an animal feedstuffs additive as a powder or granule form.

* * * * *